US011317840B2

(12) United States Patent
Youn et al.

(10) Patent No.: US 11,317,840 B2
(45) Date of Patent: May 3, 2022

(54) METHOD FOR REAL TIME ANALYZING STRESS USING DEEP NEURAL NETWORK ALGORITHM

(71) Applicant: KOREA INSTITUTE OF SCIENCE AND TECHNOLOGY, Seoul (KR)

(72) Inventors: Inchan Youn, Seoul (KR); Kuiwon Choi, Seoul (KR); Hyung Min Kim, Seoul (KR); Suh-Yeon Dong, Seoul (KR); Hyunmyung Cho, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 83 days.

(21) Appl. No.: 16/456,139

(22) Filed: Jun. 28, 2019

(65) Prior Publication Data
US 2020/0054262 A1 Feb. 20, 2020

(30) Foreign Application Priority Data
Aug. 16, 2018 (KR) .................. 10-2018-0095468

(51) Int. Cl.
*A61B 5/16* (2006.01)
*A61B 5/00* (2006.01)
*G06F 17/18* (2006.01)
*G06N 3/08* (2006.01)
*G06N 20/00* (2019.01)

(52) U.S. Cl.
CPC ............ *A61B 5/165* (2013.01); *A61B 5/4035* (2013.01); *A61B 5/746* (2013.01); *G06F 17/18* (2013.01); *G06N 3/084* (2013.01); *G06N 20/00* (2019.01)

(58) Field of Classification Search
CPC ....... A61B 5/165; A61B 5/4035; A61B 5/746; G06F 17/18; G06N 3/084; G06N 20/00
See application file for complete search history.

(56) References Cited

U.S. PATENT DOCUMENTS

| 9,962,104 | B2 | 5/2018 | De Vries et al. | |
| 2009/0069641 | A1 | 3/2009 | Cho et al. | |
| 2010/0016742 | A1 | 1/2010 | James et al. | |
| 2012/0289791 | A1* | 11/2012 | Jain .................... | A61B 5/02055 600/301 |
| 2014/0206946 | A1 | 7/2014 | Kim et al. | |

(Continued)

FOREIGN PATENT DOCUMENTS

| JP | 2006-172461 A | 6/2006 |
| JP | 2009-521246 A | 6/2009 |

(Continued)

*Primary Examiner* — Brian T Gedeon
*Assistant Examiner* — Joshua Andrew Schum-Houck
(74) *Attorney, Agent, or Firm* — Birch, Stewart, Kolasch & Birch, LLP

(57) ABSTRACT

The present invention relates to a stress analysis method including: acquiring bio-signals from a test subject; calculating a probability of each of a plurality of stress level values by processing the bio-signals using a deep neural network algorithm; estimating a stress level value with the maximum probability of the plurality of stress level values as a stress level value of the test subject; determining usefulness of the estimated stress level value; and outputting the estimated stress level value determined to be useful through the determination of usefulness, as the final stress level.

18 Claims, 7 Drawing Sheets

(56) References Cited

U.S. PATENT DOCUMENTS

| | | | |
|---|---|---|---|
| 2016/0089038 A1* | 3/2016 | Chadderdon, III | ............... A61B 5/02055 600/301 |
| 2016/0338640 A1 | 11/2016 | Chan et al. | |
| 2017/0071551 A1 | 3/2017 | Jain et al. | |
| 2017/0181700 A1 | 6/2017 | Olivier et al. | |
| 2017/0188971 A1* | 7/2017 | Liu | ............... A61B 5/316 |
| 2017/0251987 A1 | 9/2017 | Collier | |
| 2017/0316312 A1* | 11/2017 | Goyal | ............... G06N 3/0454 |
| 2017/0330029 A1* | 11/2017 | Turcot | ............... G06K 9/00308 |
| 2017/0360351 A1 | 12/2017 | Unni et al. | |
| 2018/0027158 A1* | 1/2018 | Tzvieli | ............... H04N 5/33 348/77 |
| 2018/0032689 A1 | 2/2018 | Kiranyaz et al. | |
| 2018/0078187 A1 | 3/2018 | Anwar et al. | |
| 2018/0078188 A1 | 3/2018 | Kaneko et al. | |
| 2018/0078189 A1 | 3/2018 | Chan et al. | |
| 2018/0090229 A1* | 3/2018 | Sanyal | ............... A61B 5/0024 |
| 2018/0103913 A1* | 4/2018 | Tzvieli | ............... G06K 9/4628 |
| 2018/0129893 A1* | 5/2018 | Son | ............... G06N 3/063 |
| 2018/0144214 A1* | 5/2018 | Hsieh | ............... G06K 9/036 |
| 2018/0184901 A1* | 7/2018 | Akmandor | ............... A61B 5/165 |

FOREIGN PATENT DOCUMENTS

| | | |
|---|---|---|
| KR | 10-2007-0061311 A | 6/2007 |
| KR | 10-0829822 B1 | 5/2008 |
| KR | 10-2009-0027024 A | 3/2009 |
| KR | 10-2010-0081717 A | 7/2010 |
| KR | 10-0994312 B1 | 11/2010 |
| KR | 10-1006534 B1 | 1/2011 |
| KR | 10-2012-0098365 A | 9/2012 |
| KR | 10-2012-0111242 A | 10/2012 |
| KR | 10-1223889 B1 | 1/2013 |
| KR | 10-1264156 B1 | 5/2013 |
| KR | 10-2013-0093925 A | 8/2013 |
| KR | 10-1306528 B1 | 9/2013 |
| KR | 10-1366348 B1 | 2/2014 |
| KR | 10-2014-0095291 A | 8/2014 |
| KR | 10-1664323 B1 | 10/2016 |
| KR | 10-1694251 B1 | 1/2017 |
| KR | 10-2017-0117019 A | 10/2017 |
| WO | WO 2007/096706 A2 | 8/2007 |
| WO | WO 2016/074036 A1 | 5/2016 |

* cited by examiner

METHOD FOR REAL TIME ANALYZING STRESS USING DEEP NEURAL NETWORK ALGORITHM

CROSS-REFERENCE TO RELATED APPLICATION

This application claims priority to Korean Patent Application No. 10-2018-0095468, filed on Aug. 16, 2018, and all the benefits accruing therefrom under 35 U.S.C. § 119, the contents of which in its entirety are herein incorporated by reference.

BACKGROUND

1. Field

The present invention relates to an analysis method of stress in everyday life and, more specifically, to a stress analysis method in which a stress state of a test subject is determined in real time on the basis of bio-signals measured from the test subject to output the stress state to the test subject.

DESCRIPTION ABOUT NATIONAL RESEARCH AND DEVELOPMENT SUPPORT

This study was supported by the biomedical technology development program of Ministry of Science and ICT, Republic of Korea (Projects No. 1711058668 and 1711061023) under the superintendence of National Research Foundation of Korea.

2. Description of the Related Art

Stress is considered to be a determinant of quality of life, and accumulated stress is likely to cause a variety of diseases such as depression, heart disease, and hypertension. Accordingly, the application range of a stress monitoring system is expanding for the purpose of prevention of diseases caused by stress and a health care function in everyday life.

In general, when a person is under stress, a change occurs within actions in the body. Such a change is caused by the action of an autonomic nervous system including sympathetic nerves and parasympathetic nerves.

Many studies have analyzed various bio-signals to find out the relationship between the autonomic nervous system and stress. Representative examples of bio-signals representing the change of the autonomic nervous system include electrocardiogram, electroencephalogram, skin conductivity, and the like.

In particular, the electrocardiogram is obtained by measuring electrical signals from the heart, and includes signal characteristics called the waveform of PQRST.

Specifically, when an electrocardiogram signal is used in stress analysis, variability of a heart rate called heart rate variability is used. The heart rate variability can be obtained by measuring the interval of R peaks among the electrocardiogram signal characteristics described above.

In other words, according to the prior arts, a heart rate variability parameter applied to monitor stress is calculated as a predetermined index to output a stress state at a specific time point.

However, in the conventional stress analysis method, it is possible to obtain a meaningful result of analysis about a stress state only when heart rate variability is extracted from the electrocardiogram signal of at least 5 minutes. The method includes a process of extracting R peaks from the electrocardiogram signal, and necessarily includes a preprocessing process due to vulnerability to external noise such as body movement.

In addition, since the conventional stress analysis method is the analysis of time, frequency, and nonlinear characteristics of the R peak interval of the heart rate variability, there are many cases in which the analysis result value largely depends on R peak detection performance.

In conclusion, in the conventional stress analysis method, it is practically difficult to analyze stress in real time, since various noise elimination and preprocessing steps are involved to accurately detect R peaks in everyday life in real time.

For example, as illustrated in FIG. 6, Korean Patent Publication No. 10-1006534 describes a system 1000 that extracts HRV from an electrocardiogram signal at intervals of 5 minutes, and calculates and evaluates a stress index.

In addition, as illustrated in FIG. 7, Korean Patent Publication No. 10-1264156 describes a health care system 2000 that uses a stress index acquired from HRV.

However, since the systems described in Korean Patent Publication No. 10-1006534 and Korean Patent Publication No. 10-1264156 use HRV as described above, there is a problem that it is difficult to analyze stress in real time.

RELATED ART

Korean Patent Publication No. 10-1006534
Korean Patent Publication No. 10-1264156

SUMMARY

In order to solve the problems of the prior arts described above, the invention is to provide a stress analysis method using a method of end-to-end learning through a deep neural network algorithm without the need for separate preprocessing and feature extraction such as HRV to monitor stress in everyday life of a test subject in real time.

In addition, the invention is to provide a stress analysis method customized for a test subject, in which neural network is not require additional training process due to pre-trained model and a weight is updated on the basis of electrocardiogram of a test subject.

In addition, the invention is to provide a stress analysis method that can accurately analyze a stress level of a test subject by using a plurality of bio-signals that can express change in an autonomic nervous system of a user to accurately estimate a stress level of a system.

In order to achieve the above-described technical object, the invention may provide a stress analysis method including: acquiring bio-signals from a test subject; calculating a probability of each of a plurality of stress level values by processing the bio-signals using a deep neural network algorithm; estimating a stress level value with the maximum probability of the stress level values as a stress level value of the test subject; determining usefulness of the estimated stress level value; and outputting the estimated stress level value determined to be useful through the determination of usefulness, as the final stress level.

In addition, the step of determining the usefulness of the estimated stress level value according to the invention may include determining that the estimated stress level value is useless when the probability of the estimated stress level value is less than a threshold value, receiving a recognized stress level from the test subject, applying the recognized stress level value to the deep neural network algorithm, updating the deep neural network algorithm, and repeating the stress analysis through the updated deep neural network algorithm.

In addition, the bio-signals according to the invention may be consecutive signal data, and the bio-signals may include one or more signals selected from bio-signals representing change of an autonomic nervous system including electrocardiogram, electroencephalogram, and skin conductivity.

In addition, the deep neural network algorithm according to the invention may include a convolutional neural network algorithm.

In addition, the stress analysis method according to the invention may further include informing the test subject of an alarm when the output stress level value is higher than a risk stress level value input by the test subject.

In addition, the stress analysis method according to the invention may further include storing the output stress level value in a database, statistically analyzing the values stored in the database, and outputting the result thereof.

DETAILED DESCRIPTION

Hereinafter, a stress analysis method according to the invention will be described through preferred embodiments with reference to the accompanying drawings.

In various embodiments, the same sign is used for a constituent element with the same configuration to representatively describe an embodiment, and only different constituent elements will be described for the other embodiments.

Before the description, a deep neural network algorithm used in an embodiment of the invention will be briefly described.

The deep neural network algorithm has been actively studied recently according to the development of hardware and computing algorithms, and the deep neural network algorithm is used for tasks or applications that were difficult to achieve through the existing machine learning.

Specifically, the deep neural network algorithm has a structure in which many neurons are connected to each other like a human neural network, and classifies what cannot be classified through machine learning using the deep neural network algorithm. The deep neural network algorithm is applied to many fields to increase work efficiency or to provide high quality information to a service user.

In addition, a convolutional neural network algorithm of the deep neural network algorithm is used to extract features from input data to train the fully-connected network based on the features thereafter.

Accordingly, in the following embodiment of the invention, the above-described convolutional neural network algorithm is used. As will be described later, in the embodiment of the invention, non-preprocessed bio-signals are directly input to analyze stress through the deep neural network algorithm such as the convolutional neural network.

Figure 1:
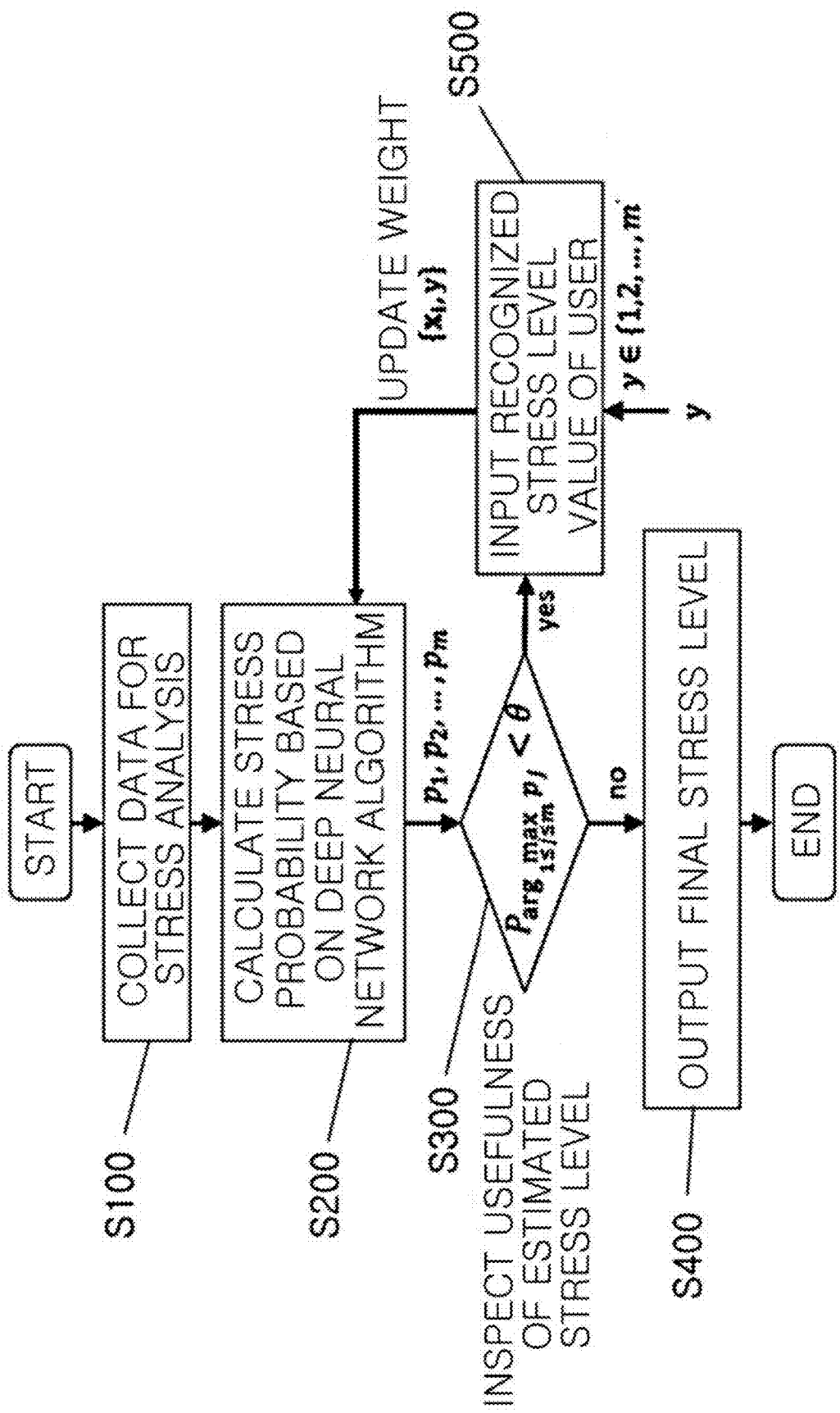
FIG. 1 is a flowchart schematically illustrating a stress analysis method according to an embodiment of the invention.

FIG. 1 is a flowchart schematically illustrating a stress analysis method according to an embodiment of the invention.

As illustrated in FIG. 1, bio-signal data of a test subject are acquired for stress level analysis of the test subject (S100). Such bio-signals may be all bio-signals which can represent autonomic nervous system activities of the test subject such as electrocardiogram, electroencephalogram, and skin conductivity.

In addition, an input value may be one or more bio-signals. For example, when an electrocardiogram is used, R peak values are detected through preprocessing and heart rate variability is extracted on the basis thereof in the related art. However, in the invention, raw bio-signals are input to a deep neural network algorithm without such a preprocessing process.

Next, a stress probability is calculated on the basis of the deep neural network algorithm (S200). The stress probability of a test subject is calculated on the basis of input data through a plurality of neural networks having respective weight.

As described above, the neural network is configured with one or more layers, and there are a plurality of neurons in one layer. In the invention, the deep neural network algorithm is utilized for stress analysis, and the final output of such a deep neural network may be a probability of each stress level.

Next, usefulness of an estimated stress level is inspected (S300). It is determined that the stress level value is not useful when the highest probability of the outputs of the deep neural network algorithm is equal to or less than a threshold value. It is possible to update the weight of the deep neural network algorithm by requesting an true label for the stress level from the test subject to adjust the weight of the deep neural network algorithm so that it fits the test subject (S500).

If the probability of the stress level value exceeds the threshold value, the stress level of the test subject can be immediately output without the update of the weight (S400). In this case, the stress level value having the highest probability among the output values of the deep neural network algorithm can be analyzed as the current stress level of the test subject.

Figure 2:
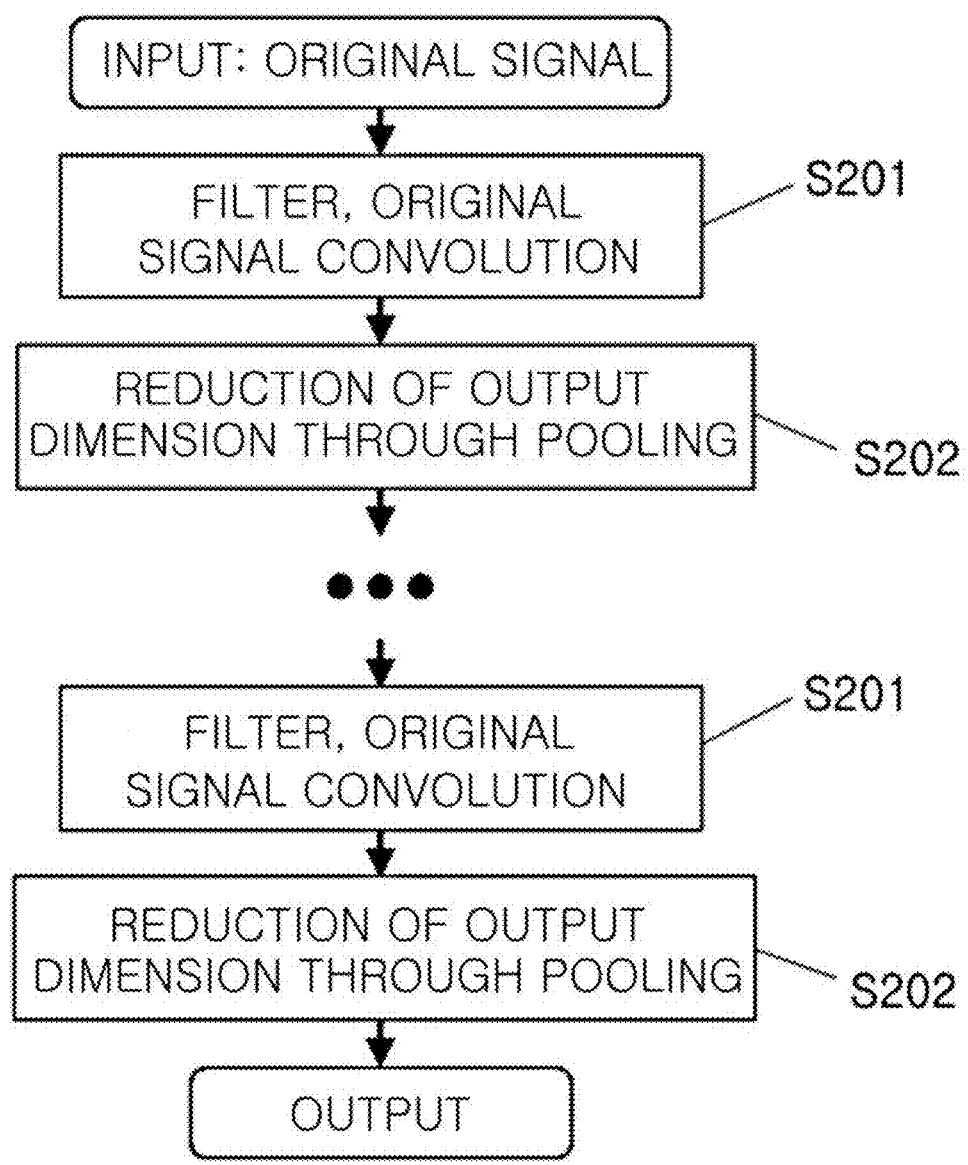
FIG. 2 and FIG. 3 are flowcharts schematically illustrating a method for measuring stress using a deep neural network algorithm in the stress analysis method according to the embodiment of the invention, in which FIG. 3 describes a method for obtaining a probability of each stress level value using values processed in FIG. 2.
Figure 3:
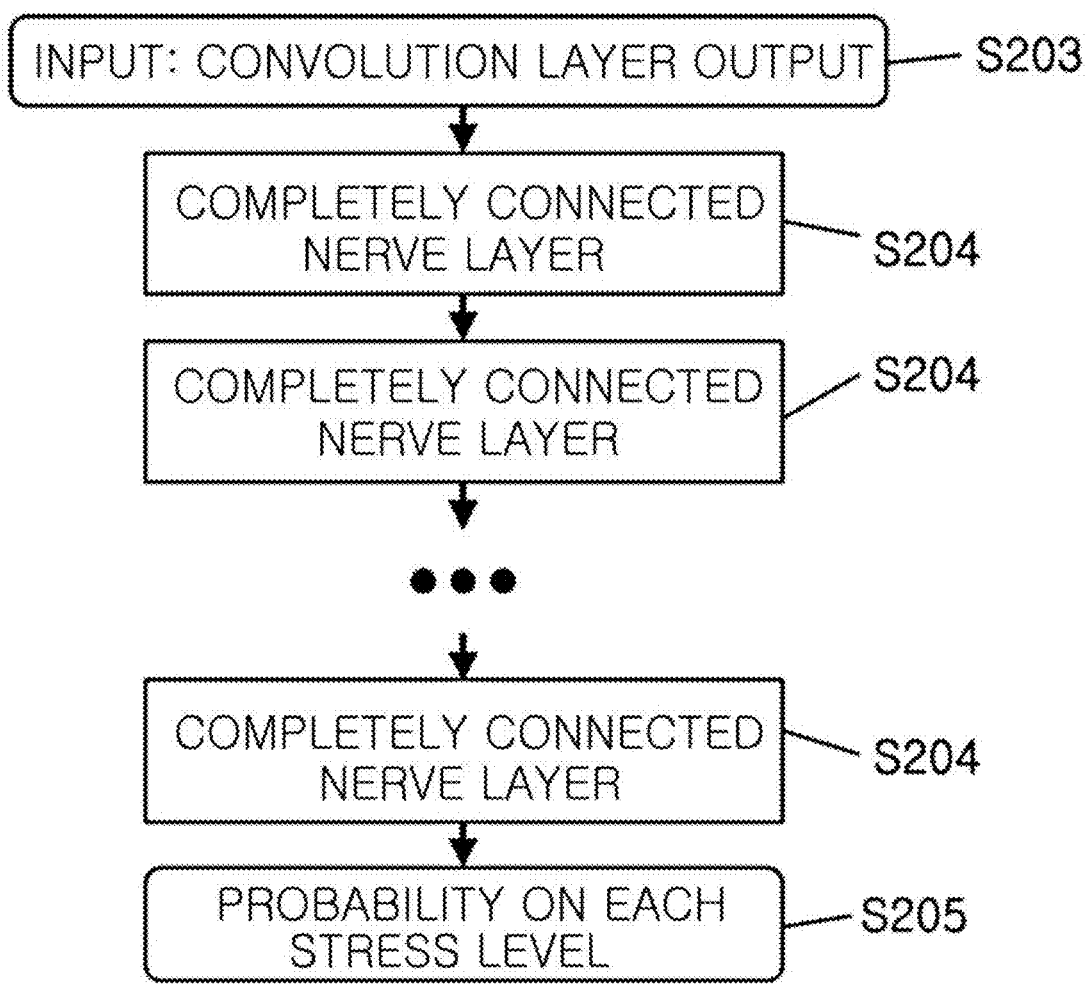

FIG. 2 and FIG. 3 are flowcharts schematically illustrating a stress analysis method using a deep neural network algorithm in the stress analysis method according to the embodiment of the invention.

As illustrated in FIG. 2 and FIG. 3, a convolutional neural network may include a convolution layer, a pooling layer, and a dense layer. A role and specific formulas in each layer will be described.

In FIG. 2, the convolution layer includes a plurality of filters each having a weight and a pooling operation. In a convolution method (S201) of the filter and original signals, original signals ($x_0, x_1, \ldots x_t$) are input to the deep neural network algorithm, and convolution of the original signals and each filter is performed as follows.

$$x \otimes w = c\{c_0, c_1, \ldots, c_m\}$$

When the convolution is performed, a movement stride of the filter may be a value of one or more. Considering signal size, movement stride, and filter size, when the desired number of outputs of the convolution is not obtained, zero-padding may be performed by adding zero to the signal.

For example, when an electrocardiogram raw signal $x=\{x_1, x_2, \ldots, x_{100}\}$ sampled for one second at 100 Hz is processed by two filters $w_1=\{w_{11}, w_{12}, w_{13}\}, w_2=\{w_{21}, w_{22}, w_{23}\}$ having a size of three, the following result may be obtained when the filter movement stride is set to one and the number of outputs is set to be equal to the length of the original signal to perform the convolution.

$$x = \{0, 0, x_1, x_2, \ldots, x_{100}\} = \{x_{-1}, x_0, x_1, x_2, \ldots x_{100}\} \text{ (zero-padding)}$$

$$x \otimes w_1 = \sum_{i=1}^{3} x_{i+j} w_{1i} = c_1 - 2 \leq j \leq 97$$

$$x \otimes w_2 = \sum_{i=1}^{3} x_{i+j} w_{2i} = c_2 - 2 \leq j \leq 97$$

$$c = \{c_1, c_2\}, \text{shape} = (2, 100)$$

Next, the dimension of the output of the convolution is reduced through the pooling operation (S202). The pooling operation may be maximum value pooling and average value pooling. The maximum value pooling returns the largest value of incoming input values, and the average value pooling returns an average value of the inputs. The incoming input values are returned as one of the maximum value or the average value to reduce the dimension of the input values.

For example, when the maximum value pooling operation with an input dimension=(2, 100), a pooling window of 5, and a pooling window movement stride of 5 is performed, the following result may be obtained.

$$pooling_1^1 = \max(\{c_1^1, c_2^1, c_3^1, c_4^1, c_5^1\})$$

$$\ldots$$

$$pooling_{20}^1 = \max(\{c_{96}^1, \ldots, c_{100}^1\})$$

$$pooling_1^2 = \max(\{c_1^2, \ldots, c_5^2\})$$

$$\ldots$$

$$pooling_{20}^2 = \max(\{c_{96}^2, \ldots, c_{100}^2\})$$

Finally, it is possible to see reduction from the dimension (2, 100) to the dimension (2, 20).

In short, as illustrated in FIG. 2, it is possible to extract features of signals using the neural network from the raw signals through the overlapping convolution and pooling operation. The convolution of original signal or the output of the previous operation and the filter is performed to extract the features and the dimension of the input is reduced through pooling operation, finally thereby reducing the number of dimensions of the input incoming to the dense layer illustrated in FIG. 3 and reducing the operation necessary therein.

In FIG. 3, the dense layer receives the output value of the convolution layer as the input value. The output value of the convolution layer means features extracted from the raw signal and the output value with the dimension reduced through the pooling.

The extracted features are learned to a completely connected neural layer each of which has a weight and in which all neurons are connected, to finally obtain a probability for each stress level value (S205).

For example, when the output of k stress levels, two completely connected neural layers, and the convolution layer is $$c = \begin{bmatrix} c_1^1 & \cdots & c_{20}^1 \\ c_1^2 & \cdots & c_{20}^2 \end{bmatrix},$$

the following operation is performed.

$$c = [c_1^1, c_2^1, \ldots, c_{20}^1, c_1^2, \ldots c_{20}^2] = [c_1, c_2, \ldots, c_{40}], \text{shape} = (1, 40)$$

$$1st\ FC\ \text{layer} = \begin{bmatrix} w_1^1 & \cdots & w_j^1 \\ \vdots & \ddots & \vdots \\ w_1^{40} & \cdots & w_j^{40} \end{bmatrix}, \text{shape} = (40, j)$$

$$2nd\ FC\ \text{layer} = \begin{bmatrix} w_1^1 & \cdots & w_k^1 \\ \vdots & \ddots & \vdots \\ w_1^j & \cdots & w_k^j \end{bmatrix}, \text{shape} = (j, k)$$

output layer = input $*$ FC layer $*$ 2nd FC layer, shape = (1, k)

output layer = $\{p_1, p_2, \ldots, p_k\}$ (k-level stress)

In other words, a stress level value with the highest probability of a set $\{p_1, p_2, \ldots, p_k\}$ having a probability for k stress levels may be estimated as a current stress level value of the test subject.

Figure 4:
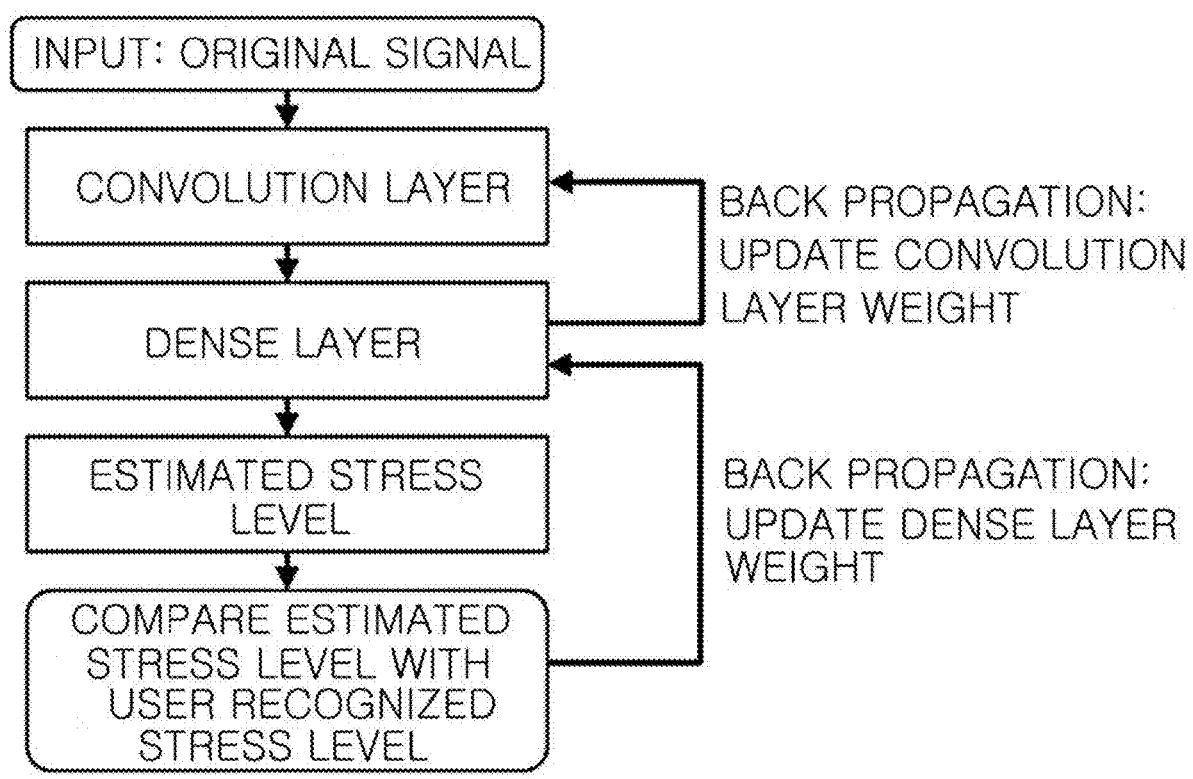
FIG. 4 is a flowchart schematically illustrating that an estimated stress level value of a test subject is applied to the deep neural network algorithm in the stress analysis method according to the embodiment of the invention.

FIG. 4 is a flowchart schematically illustrating that an estimated stress level value of a test subject is applied to the deep neural network algorithm in the stress analysis method according to the embodiment of the invention.

As illustrated in FIG. 4, according to the invention, stress of a test subject is estimated on the basis of the deep neural network algorithm. Since a stress degree may vary according to personal characteristics, stress of the test subject may not be accurately estimated through the learned deep neural network algorithm.

Accordingly, in the case of $$P_{\arg\max_{1 \leq j \leq m} p_j} < \theta$$

for a critical point θ, a true label for the stress level is received from the test subject, and the weight can be newly updated as customization for the test subject. Specifically, the weight of the neural network algorithm with a preceding weight can be changed by comparing the estimated stress level value with the recognized stress level value of the test subject. A function used in the comparison may use various types of comparison (cost) formulas, and the weight of the deep neural network algorithm can be updated such that the function gets closer to zero.

For example, in the case of a cross-entropy function, when the estimated stress level value is H(x) and the recognized stress level value input from the test subject is y, the comparison value (cost) is defined as cost=−[yln(H(x))+ln(1−H(x))], the weight value is updated such that the comparison value (cost) is zero through error back propagation, to finally configure the deep neural network algorithm customized for the test subject.

Figure 5:
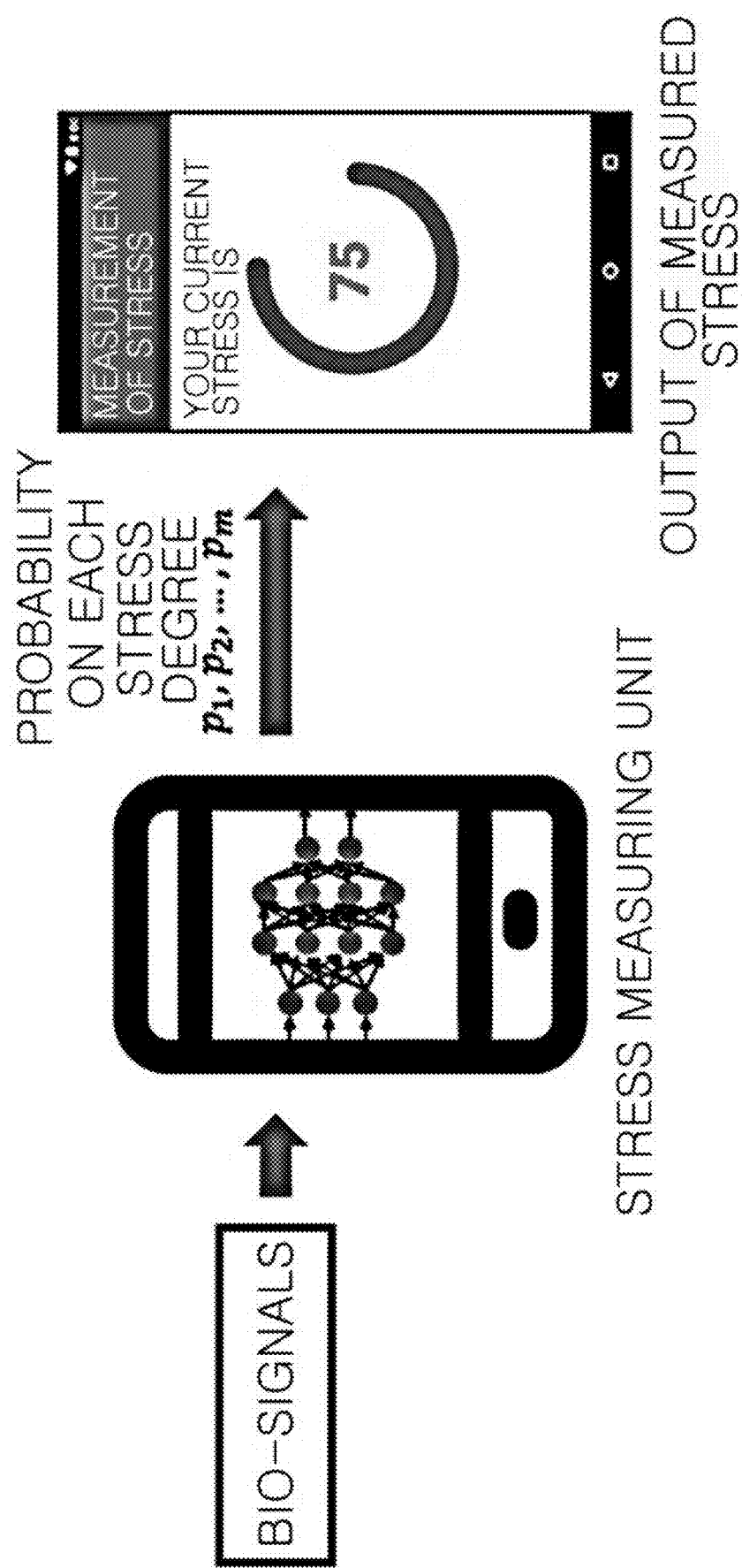
FIG. 5 is a diagram schematically illustrating that the stress analysis method according to the embodiment of the invention is applied to a mobile device to output a stress index.
Figure 6:
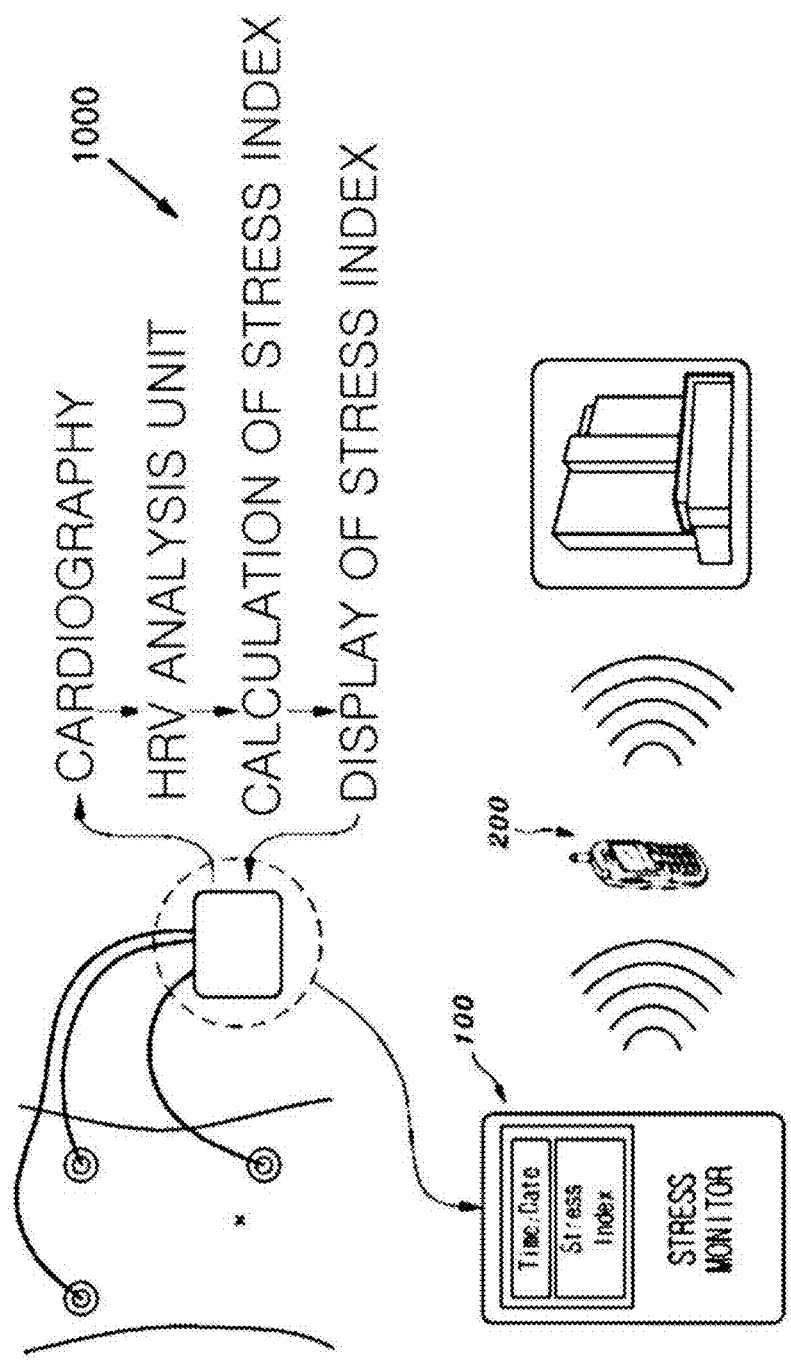
FIG. 6 is a diagram schematically illustrating a conventional stress analyzing system according to Korean Patent Publication No. 10-1006534.
Figure 7:
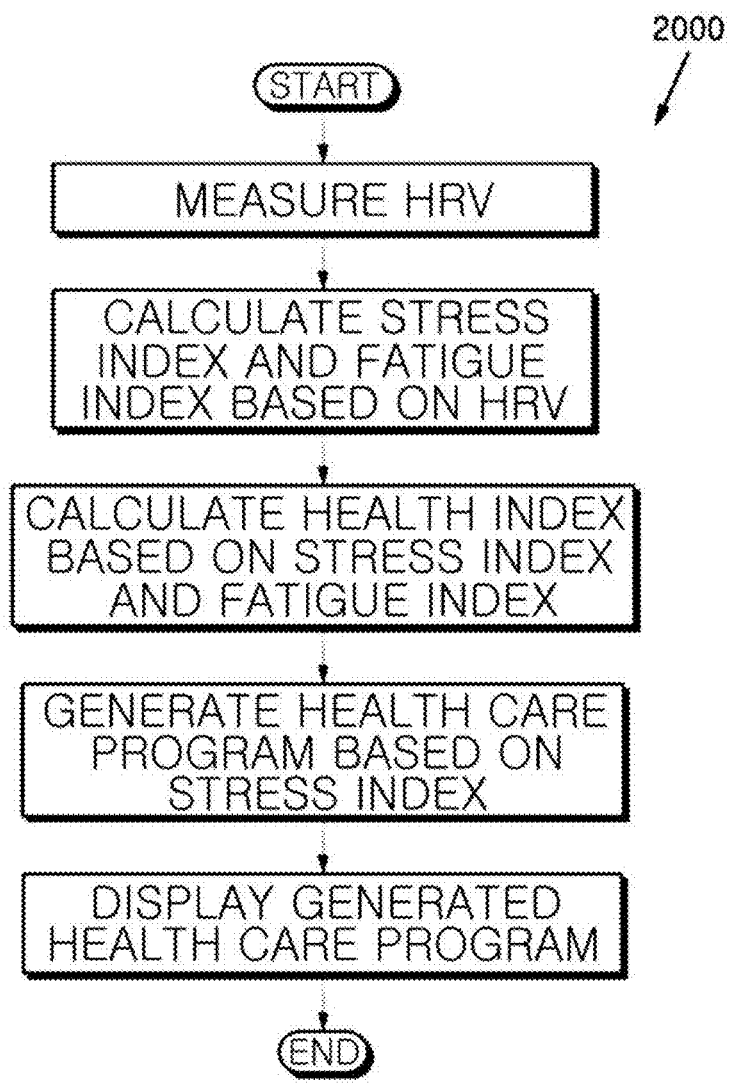
FIG. 7 is a diagram schematically illustrating a conventional stress analyzing system according to Korean Patent Publication No. 10-1264156.

FIG. 5 is a diagram schematically illustrating that the stress analysis method according to the embodiment of the invention is applied to a mobile device to output a stress index.

As illustrated in FIG. 5, the analysis method based on the deep neural network algorithm is applied to a mobile device so that it is possible to display the current stress of the test subject by receiving the bio-signals of the test subject. Such a mobile device can receive the bio-signals, analyze stress, and output the measured stress level value.

Specifically, in order to collect data for measurement of stress from a sensor, for example, in the case of an electrocardiogram, the electrocardiogram is measured in the chest and the corresponding raw signal can be transmitted to the mobile device through Bluetooth or other wireless communication.

In addition, in order to analyze stress of the test subject based on bio-signals, the bio-signals transmitted from the sensor are transmitted to the mobile device and the raw signals are input to the deep neural network algorithm of the invention as they are. As with the description above, the stress level value is measured on the basis of the deep neural network algorithm, and the probability for each stress level is obtained as a result value.

In addition, the highest level of probabilities for stress levels obtained through a mobile application is selected to display the current stress level value of the test subject.

Meanwhile, in order to inspect the usefulness of the input data, when the highest value of the probabilities of the stress levels is smaller than a set threshold value, the test subject may be required to input a stress degree which the test subject feels currently through the application.

The test subject inputs the stress level value currently recognized by the test subject, and the deep neural network algorithm receives the value and updates the weight according to the test subject.

Subsequently, since the stress can be analyzed on the basis of the updated deep neural network algorithm as described above, it is possible to accurately analyze the stress by learning the state of the test subject.

According to the invention, it is possible to use a stress measuring system learned with a bio-signal database as an initial model of a deep neural network algorithm, and it is possible to provide a stress analysis method which can update a learning weight as a customized system when bio-signals of a test subject start to be input.

In addition, according to the invention, for efficient system update, it is possible to execute system update using only input data useful for weight update.

In addition, according to the invention, it is possible to build a system that can be implemented in a mobile or portable device without a separate server or device.

What is claimed is:
1. A method of controlling a mobile device, the method comprising:
receiving, via a wireless interface, raw bio-signals of a test subject from a sensor;
inputting the raw bio-signals into a convolution layer of a deep neural network algorithm having one or more filters to extract features from the raw bio-signals and generate an output dimension;
inputting the output dimension to a pooling layer of the deep neural network algorithm to generate a reduced dimension;
inputting the reduced dimension to a dense layer of the deep neural network algorithm having one or more neural layers each having a weight and connected neurons, and generating a probability of each of a plurality of stress level values based on processing the reduced dimension using the weight and the connected neurons;
estimating a stress level value with a maximum probability of the plurality of stress level values as a stress level value of the test subject;
determining that the estimated stress level value is useful based on a set threshold value; and
displaying, via a display of the mobile device, the estimated stress level value determined to be useful as an output stress level,
wherein the output stress level is a score or percentage indicating an amount of stress experienced by the test subject,
wherein the determining that the estimated stress level value is useful includes:
determining that the estimated stress level value is useless when the maximum probability of the plurality of stress level values is less than the set threshold value,
in response to determining that the estimated stress level value is useless, requesting that the test subject input a recognized stress level,
in response to receiving the recognized stress level value input by the test subject, applying the recognized stress level value to the deep neural network algorithm,
updating the deep neural network algorithm to generate an updated deep neural network algorithm, and
performing stress analysis through the updated deep neural network algorithm.
2. The method according to claim 1, wherein the raw bio-signals are consecutive signal data.
3. The method according to claim 2, wherein the raw bio-signals include one or more signals selected from raw bio-signals representing change of an autonomic nervous system including electrocardiogram, electroencephalogram, and skin conductivity.
4. The method according to claim 1, wherein the deep neural network algorithm includes a convolutional neural network algorithm and the convolution layer and the pooling layer are included in the convolutional neural network algorithm.
5. The method according to claim 1, further comprising informing the test subject of an alarm when the output stress level value is higher than a risk stress level value input by the test subject.
6. The method according to claim 1, further comprising storing the output stress level value in a database, statistically analyzing values stored in the database, and outputting a result thereof.

7. The method according to claim 1, wherein the deep neural network algorithm is stored in a memory of the mobile device.

8. The method according to claim 1, wherein the pooling layer is connected between the convolution layer and the dense layer.

9. The method according to claim 1, wherein the method is performed in real time.

10. The method according to claim 1, wherein the raw bio-signals are non-preprocessed bio-signals that are directly input to the deep neural network algorithm.

11. A mobile device, comprising:
a display configured to display information;
a wireless interface configured to receive raw bio-signals of a test subject from a sensor; and
a processor configured to:
input the raw bio-signals into a convolution layer of a deep neural network algorithm having one or more filters to extract features from the raw bio-signals and generate an output dimension,
input the output dimension to a pooling layer of the deep neural network algorithm to generate a reduced dimension,
input the reduced dimension to a dense layer of the deep neural network algorithm having one or more neural layers each having a weight and connected neurons, and generate a probability of each of a plurality of stress level values based on processing the reduced dimension using the weight and the connected neurons,
estimate a stress level value with a maximum probability of the plurality of stress level values as a stress level value of the test subject;
determine that the estimated stress level value is useful based on a set threshold value,
determine that the estimated stress level value is useless when the maximum probability of the plurality of stress level values is less than the set threshold value,
in response to determining that the estimated stress level value is useless, request that the test subject input a recognized stress level,
in response to receiving the recognized stress level value input by the test subject, apply the recognized stress level value to the deep neural network algorithm,
update the deep neural network algorithm to generate an updated deep neural network algorithm,
perform stress analysis through the updated deep neural network algorithm, and
display, via the display, the estimated stress level value determined to be useful as an output stress level,
wherein the output stress level is a score or percentage indicating an amount of stress experienced by the test subject.

12. The mobile device according to claim 11, further comprising a memory configured to store the deep neural network algorithm.

13. The mobile device according to claim 11, wherein the raw bio-signals are consecutive signal data.

14. The mobile device according to claim 13, wherein the raw bio-signals include one or more signals selected from bio-signals representing change of an autonomic nervous system including electrocardiogram, electroencephalogram, and skin conductivity.

15. The mobile device according to claim 11, wherein the deep neural network algorithm includes a convolutional neural network algorithm and the convolution layer and the pooling layer are included in the convolutional neural network algorithm.

16. The mobile device according to claim 11, wherein the processor is further configured to output an alarm or notification informing the test subject that the output stress level value is higher than a risk stress level value input by the test subject.

17. The mobile device according to claim 11, wherein the processor is further configured to store the output stress level value in a database, statistically analyze values stored in the database, and output a result thereof.

18. The mobile device according to claim 11, wherein the raw bio-signals are non-preprocessed bio-signals that are directly input to the deep neural network algorithm.

* * * * *